(12) United States Patent
Formstone et al.

(10) Patent No.: US 7,994,095 B2
(45) Date of Patent: Aug. 9, 2011

(54) ANTIFOAMING FORMULATIONS

(75) Inventors: Carl Formstone, Guildford (GB); James Hogbin, Guildford (GB); Rowena Landham, Guildford (GB); Daniel Lipin, St. Lucia (AU); Rupert Sohm, Muenchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 811 days.

(21) Appl. No.: 10/553,914

(22) PCT Filed: May 27, 2004

(86) PCT No.: PCT/US2004/016714
§ 371 (c)(1), (2), (4) Date: Dec. 21, 2006

(87) PCT Pub. No.: WO2004/105914
PCT Pub. Date: Dec. 9, 2004

(65) Prior Publication Data
US 2007/0179077 A1  Aug. 2, 2007

(30) Foreign Application Priority Data

May 28, 2003 (GB) .................................. 0312195.1

(51) Int. Cl.
*A01N 25/04* (2006.01)
*A01N 25/18* (2006.01)
*A01N 43/60* (2006.01)
*A01N 43/42* (2006.01)
*A01N 43/40* (2006.01)
*A01N 43/48* (2006.01)
*A01N 37/10* (2006.01)
*A01N 37/02* (2006.01)
*B01D 19/04* (2006.01)
*A01N 25/00* (2006.01)
*B01D 19/02* (2006.01)

(52) U.S. Cl. ........ 504/363; 504/364; 504/201; 504/204; 504/235; 504/247; 504/253; 504/314; 504/323; 504/116.1; 516/121; 516/123; 516/124

(58) Field of Classification Search .................. 516/121, 516/123, 124; 504/364, 201, 204, 235, 247, 504/250, 253, 314, 323, 363, 116.1
See application file for complete search history.

(56) References Cited

U.S. PATENT DOCUMENTS

| | | | | |
|---|---|---|---|---|
| 2,865,859 A | * | 12/1958 | Lubowe | 508/505 |
| 3,185,627 A | * | 5/1965 | Kass | 514/785 |
| 3,210,248 A | * | 10/1965 | Feldmann et al. | 514/170 |
| 3,392,040 A | * | 7/1968 | Kass | 106/287.13 |
| 4,338,217 A | * | 7/1982 | Pirson et al. | 516/118 |
| 4,940,574 A | * | 7/1990 | Kaplan | 424/59 |
| 5,200,550 A | * | 4/1993 | Shroot et al. | 560/64 |
| 5,252,761 A | * | 10/1993 | Hirose et al. | 554/77 |
| 5,397,766 A | * | 3/1995 | Dexter | 504/128 |
| 5,405,825 A | * | 4/1995 | Baker | 504/139 |
| 5,531,929 A | | 7/1996 | Kobayashi | |
| 5,573,769 A | * | 11/1996 | Creech et al. | 424/403 |
| 5,968,872 A | * | 10/1999 | Policello et al. | 516/124 |
| 6,087,403 A | * | 7/2000 | Bertho et al. | 516/72 |
| 6,162,764 A | | 12/2000 | Atkinson et al. | |
| 6,165,939 A | * | 12/2000 | Agbaje et al. | 504/105 |
| 6,221,922 B1 | * | 4/2001 | Policello et al. | 516/118 |
| 6,365,211 B1 | * | 4/2002 | Corrigan | 426/116 |
| 6,403,163 B1 | | 6/2002 | Fisher et al. | |
| 6,417,140 B1 | * | 7/2002 | Patel | 504/127 |
| 6,451,731 B1 | * | 9/2002 | Agbaje et al. | 504/118 |
| 2002/0147111 A1 | * | 10/2002 | Sun | 504/366 |
| 2003/0072776 A1 | * | 4/2003 | Sun et al. | 516/117 |
| 2004/0086540 A1 | * | 5/2004 | Campbell et al. | 424/405 |
| 2005/0164884 A1 | | 7/2005 | Bramati et al. | |

FOREIGN PATENT DOCUMENTS

WO  03065803  8/2003

OTHER PUBLICATIONS

SAG* 47 Foam Control Agent/NI/998KG, Momentive Performance Materials Inc., online @ http://www.momentive.com/Internet/Silicones/Brand/SAG*/SAG*+47+Antifoam+Compound?productid=218f049e405bc110VgnVCM1000000942515ac_, (Version Jun. 18, 2008), (downloaded Sep. 2009), pp. 1-7.*

Silicones Rhodorsil Rhodorsil ® OILS 47 V 50 to 47 V 1000, (Dec. 1996) Technical Data Sheet, Rhodia, Chimie, obtained online @ http://www.bentleychemicals.co.uk/files/47y50_-_1000_1.pdf (downloaded Sep. 5, 2010) pp. 1-4.*

Product Information Healthcare, Dow Corning® ST-Cyclomethicone 5-NF, Dow Corning Corporation ( May 21, 2009) Obtained online @ http://www3.dowcorning.com/DataFiles/090007c88020e2df.pdf (downloaded Sep. 5, 2010) pp. 1-5.*

V. Bergeron et al, "Polydimethylsiloxane (PDMS)-based antifoams", Colloids and Surfaces A: Physicochemical and Engineering Aspects 122 (Apr. 14, 1997) 103-120, obtained online@http://www.sciencedirect.com/ , (downloaded Sep. 6, 2010).*

* cited by examiner

*Primary Examiner* — Daniel S Metzmaier
(74) *Attorney, Agent, or Firm* — Rebecca Howard

(57) ABSTRACT

Aqueous concentrates and aqueous compositions (e.g., agrochemical) containing a water-insoluble liquid antifoam agent (e.g., liquid silicone-containing antifoam agent) are disclosed. The water-insoluble liquid antifoam agent is incorporated into the concentrate or composition as a solution of the water-insoluble liquid antifoam agent solubilized in an organic solvent (e.g., isopropyl myristate, butyl cocoate or butyl laurate).

21 Claims, No Drawings

ANTIFOAMING FORMULATIONS

This invention relates to a formulation, and in particular to an improved formulation containing a water-insoluble liquid antifoam agent.

Antifoam agents are commercially available to minimize problems of the foaming of surfactant-containing aqueous compositions. A typical application is in respect of aqueous agrochemical formulations supplied as concentrates and intended to be diluted prior to application. Such concentrates generally contain surfactants, which may be incorporated for a variety of purposes, including for example bio-performance enhancement (the enhancement of any property which either directly or indirectly improves agrochemical activity). The presence of surfactants in agrochemical concentrates frequently tends to promote foaming which may take place either in the bottle/container, or on the addition of the concentrate to water in a spray tank or if the spray tank containing the diluted formulation is transported to the site where the agrochemical is to be applied. The presence of residual foam can also cause problems if a spray tank is re-filled with the same product without thorough clean down between each re-fill. In general, different antifoam compositions are used to protect against foaming of the bulk concentrate ("bulk defoamers") and against foaming of the concentrate on dilution or once diluted. Commercial antifoam compositions directed to the problem of foaming of the concentrate on dilution or once diluted are typically water-insoluble oils such as (poly) alkyl silicones. It is believed that that the antifoam oil absorbs strongly at the air/water/surfactant interface and reduces the energy of the interface thereby limiting foaming. Hydrophobic silica may also be incorporated and has the effect of binding to and disrupting the air/water/surfactant interface. Whatever the exact mechanism of the operation of such water-insoluble oil antifoams, they are effective when present at a suitable concentration.

Water-insoluble antifoam oils however suffer from the disadvantage that they separate rapidly from any aqueous system if there is a density difference between the oil/aqueous phases. Stokes Law describes this separation mathematically in terms of any density differences between the phases.

Equation 1: Stokes Law $$u_{disp} = \frac{g d_{disp}^2 (\rho_{disp} - \rho_{cont})}{72 \mu_{cont}}$$

$U_{disp}$ Velocity of dispersed droplet (m s$^{-1}$)
g Acceleration due to gravity (m s$^{-2}$)
$d_{disp}$ Diameter of dispersed droplet (m)
$\rho_{disp}$ Density of dispersed droplet (kg m$^{-3}$)
$\rho_{cont}$ Density of continuous phase (kg m$^{-3}$)
$\mu_{cont}$ Viscosity of continuous phase (kg s$^{-1}$ m$^{-1}$)

This is not a major problem if the antifoam is incorporated into a formulation and is immediately bottled into unit-dose containers whose contents are added all at once to a spray tank. Frequently however an agrochemical formulation is stored for extended periods of time in bulk, either by the farmer or a distributor. When the desired portion is drawn off for use any separation of the antifoam means that the resultant product either contains too much antifoam or essentially none at all. We have found that conventional antifoam systems can separate from the bulk aqueous medium completely in as little as from 2 to 24 hours, as confirmed by invoking Stokes Law using typical parameters. It would be possible to stir the contents of the bulk storage facility to re-disperse and homogenise the antifoam prior to drawing off product, but even if it were practicable to provide an effective stirring mechanism, this would involve considerable additional expense.

Antifoam products are also supplied as emulsions in which the oil is emulsified into water. For example commercial emulsions of antifoams typically contain from 10 to 50% silicone oil and are generally more easily handled than the relatively viscous antifoam oil itself. We have found however that such commercially available emulsions are not effectively incorporated into aqueous agrochemical concentrates and undergo rapid separation of the antifoam.

We have now found that the problem of separation of antifoam may be overcome or mitigated, if the antifoam is dissolved in a suitable solvent prior to incorporation in the aqueous formulation.

According to the present invention there is provided an aqueous composition comprising a water-insoluble liquid antifoam agent wherein the antifoam agent is incorporated into the composition as a solution in an organic solvent.

The aqueous composition is preferably an aqueous agrochemical composition, for example an aqueous solution of a water-soluble agrochemical or an aqueous dispersion of a water-insoluble solid agrochemical or an aqueous emulsion of a water-insoluable liquid agrochemical. The aqueous composition is generally an aqueous agrochemical concentrate intended for dilution prior to use. The aqueous agrochemical composition will generally contain surfactants, for example bio-performance enhancing surfactants, which tend to induce foaming and hence require the presence of an antifoam agent. The term bioperformance enhancing surfactant as used herein includes any surfactant that improves the biological activity of the agrochemical, either directly or indirectly.

Thus according to a further aspect of the present invention there is provided an aqueous composition comprising an agrochemical one or more foam-inducing surfactants and a water-insoluble antifoam agent wherein the antifoam agent is incorporated into the composition as a solution in an organic solvent.

In one embodiment the agrochemical is a water-soluble agrochemical.

A further aspect of the invention is directed to a method for reducing or eliminating the separation of a water-insoluble antifoam in an aqueous agrochemical composition, said method comprising introducing a water-insoluble antifoam into the aqueous agrochemical composition in the form of a solution in an organic solvent.

The action of the solvent is complex and poorly understood but it appears to have the overall effect of improving the dispersability of the antifoam oil in the aqueous medium of the agrochemical concentrate. In terms of its interaction with pure water, the solvent for the antifoam agent may be water immiscible, water miscible or partially water-miscible. We have found however that even solvents that appear to be largely immiscible with water (such that mixtures with tap or de-ionised water separate very rapidly) may disperse surprisingly effectively in the aqueous medium of the agrochemical concentrate.

Suitably the solubility of the antifoam agent in the solvent is at least 10% by weight at typical room temperature (15-20° C.). Whilst there is no upper limit on the solubility of the antifoam agent in the solvent, we have found that few solvents can provide a solubility of greater than 30% at room temperature. In view of the limited solubility of the antifoam agent in solvents useful in the present invention, it is preferred that the solution of the antifoam agent in the solvent approaches the solubility (miscibility) limit The solvent is suitably selected such that the solubility (miscibility) limit of the antifoam oil in the solvent is at least 10% by weight and preferably at least 12% by weight, for example at least 15%. Typical solubility ranges are thus from about 10% by weight to about 30% by weight, for example from about 10% by weight to about 20% by weight and more particularly from 12% by weight to about 18% by weight. The concentration of the antifoam oil in the solvent is then preferably at or near its solubility (miscibility) limit.

The antifoam oil is typically incorporated in the aqueous agrochemical concentrate at a level of about 0.1 to 10 g/l and more typically 0.3 to 3 g/l, for example 0.4 to 1.4 g/l. The proportion of the solution of the antifoam added to the aqueous medium is therefore determined by the concentration of the antifoam in the solvent and the desired level of antifoam to be provided in the aqueous concentrate.

Antifoam agents may be used in a variety of aqueous compositions of agrochemicals including suspension or emulsion concentrates of water-insoluble agrochemicals and the present invention is applicable to both water-soluble and water-insoluble agrochemicals. Separation problems may be more often encountered however in compositions containing water-soluble agrochemicals. Examples of water-soluble agrochemicals useful in the composition of the present invention include glyphosate, paraquat, diquat, dicamba, fomesafen, imazethapyr, imazaquin, imazapyr, 2,4-D, and glufosinate. Mixtures of agrochemicals may also be used, including for example mixtures of glyphosate and dicamba and mixtures of glyphosate and diquat. Numerous other examples of suitable agrochemicals and mixtures of agrochemicals are listed in standard works of reference and will occur to those skilled in the art. Where appropriate, the acidic agrochemicals are suitably used in the form of their water-soluble salts.

The antifoam agent is typically based on a silicone active material such as a polyalkylsilicone active material, for example a polydimethylsilicone oil or a derivative thereof, either alone or in combination with additives such as hydrophobic silicas.

Numerous commercially available antifoam agents are available and examples include:
Silicone S 203 antifoam (Wacker); Antifoam A and Antifoam MSA (Dow Corning); Antifoam DB100 (Dow Corning); SAG-47, SAG-710 and SAG-100 (Crompton); and "Rhodasil" 454, 422, FD (Rhodia)

A particular example of a typical and suitable antifoam agent is Antifoam MSA (MSA is a tradename of Dow Corning) (density 0.98 g/ml), which consists of a proprietary blend of polydimethylsilicone oil and hydrophobic silicas.

All densities given herein are quoted as measurements at room temperature (20° C.). It will be appreciated that the application of Stokes law would indicate that, even for a well-dispersed system, an additional factor in the rate of separation of the antifoam oil is the magnitude of the density difference between the antifoam and the aqueous medium of the agrochemical concentrate. The density of a typical antifoam is about 1 g/ml, whilst that of a typical agrochemical concentrate is normally above 1 g/ml, for example up to 1.4 g/ml. This density difference is an important factor in driving the separation of even a well-dispersed antifoam system over an extended period of time (the so-called "creaming" effect).

The presence of the solvent will influence the density of the antifoam oil system and indeed the benefits of effective dispersion may to some extent be offset if the solution of the antifoam agent in the solvent is greatly below 1 g/ml. Conversely a solvent giving a solution of the antifoam a density greater than 1 g/ml may prove beneficial if the density is brought closer to that of the aqueous concentrate medium. It is not essential that the solvent provides a solution of the antifoam agent in which the density exactly matches that of aqueous agrochemical medium, but it is preferred that the density of the solution of the antifoam agent in the solvent is not significantly less than that of the antifoam agent alone, for example not more than 0.2 g/ml less than that of the antifoam agent alone. It is especially preferred therefore that the solvent is selected such that density of the solution of the antifoam agent in the solvent (the solution density) is from 0.8 to 1.5 g/ml.

When the density of the solution of the antifoam in the solvent is below that of the aqueous concentrate medium, solvents providing solutions having densities of, for example from 0.8 to 1.1 g/ml, generally provide entirely satisfactory results. Where such solvents have significant other advantages in the context of a practical agrochemical concentrate composition (as discussed in more detail below) a solvent giving rise to a solution density of 0.8 to 1.1 g/ml is entirely acceptable even if the density is below that of the aqueous concentrate medium.

It is possible (but as noted above not essential) to select a solvent such that density of the solution of the antifoam in the solvent more is closely matched to that of the aqueous medium of the agrochemical concentrate.

In one embodiment of the present invention therefore, the solvent further decreases the tendency of the antifoam agent to separate from the aqueous medium by reducing the density difference between the antifoam agent and the aqueous medium of the agrochemical concentrate.

The density of the aqueous agrochemical solution will vary depending on the nature of the agrochemical and other contents of the formulation, but as previously noted is generally greater that 1 g/ml. Thus a glyphosate concentrate containing from 180 to 540 g/l active ingredient based on glyphosate acid typically has a density from about 1.1 to 1.4 g/ml, and more commonly a density from 1.2 to 1.4 g/ml. A paraquat concentrate containing from 100 to 360 g/l active ingredient based on paraquat ion typically has a density of about 1.1 g/ml. A diquat concentrate containing from 100 to 360 g/l active ingredient typically has a density of about 1.1 g/ml.

It may be possible one aspect of the invention to provide a solvent according to the present invention such that the density of the solution of the antifoam agent in the solvent differs from that of the agrochemical formulation by no more than 0.1, for example no more than 0.05 g/l density units.

Thus according to a further aspect there is provided an aqueous concentrate composition comprising a water-soluble agrochemical, one or more foam-inducing surfactants and an antifoam agent wherein the antifoam agent is incorporated into the composition as a solution in an organic solvent and wherein the solvent is selected such that the density of the solution of the antifoam agent in the solvent differs from the density of the aqueous concentrate composition measured in the absence of solvent and antifoam by not more than 0.1 g/l density units, all density measurements being conducted at room temperature.

There will be even less tendency for the antifoam agent to separate by creaming if the solvent is selected such that the density of the solution of the antifoam agent in the solvent differs from the density of the aqueous concentrate composition measured in the absence of solvent and antifoam by not more than 0.05 g/l density units.

Given the typical densities of the aqueous agrochemical concentrates quoted above, a solvent selected such that the density of the solution of the antifoam agent in the solvent differs from the density of the aqueous concentrate composition measured in the absence of solvent but in the presence of antifoam agent by not more than 0.1 g/l density units or more particularly by not more that 0.05 g/l density units will generally also provide a solution having a density within the range 0.8 to 1.5 g/ml.

Clearly, if it is intended to match the density of the aqueous agrochemical concentrate, the preferred solvent will vary depending on the density of the particular composition concerned. For agrochemical compositions having densities in the 1.2 to 1.4 g/ml range, for example typical glyphosate compositions, examples of suitable solvents which provide solutions to "match" the density of the composition include 1-bromobenzene (density 1.49 g/ml); 1-bromopropane (density 1.22 g/ml); 2-bromopropane (density 1.35 g/ml); 1-bromopentane (density 1.31 g/ml); cyclohexyl bromide (density 1.32 g/ml); glycerol formal (density 1.20 g/ml); and 2,2,3,3-tetrafluoro-1-propanol (density 1.26 g/ml). The density of the solution of the antifoam agent at the required concentration may be readily determined, but will not in general differ from that of the solvent itself by more than 0.1 density units. We have found that a typical silicone antifoam was sufficiently soluble in all the above-mentioned solvents to give a solution containing 16% antifoam by weight. Clear or slightly cloudy mixtures were obtained for all solvents except glycerol formal and 2,2,3,3-tetrafluoro-1-propanol, which showed a tendency to separate and are therefore less preferred.

The use of solvents for the antifoam agent having low volatility and flammability preclude any danger of explosion in the bulk preparation or the composition or in the storage tank. Suitably therefore the flash point of the solvent is greater than 40° C. Solvents with lower flash points can be accommodated however provided that suitable safety systems are incorporated in the bulk preparation stage or storage tank. Thus for example, whilst 2-bromopropane is an eminently suitable solvent if it is desired to match the density of an aqueous agrochemical concentrate having a density of about 1.35 g/ml, it has a relatively low flash point of 22° C. and would require special handling.

Solvents suitable for use in the present invention which may be used without a requirement for special handling are therefore characterised by (a) an ability to dissolve a typical silicone antifoam such as Antifoam MSA to the extent of greater than 12% by weight, for example greater than 15% by weight; (b) a solution density of greater than 0.8 g/ml, for example from 0.8 to 1.1 g/ml; and (c) a flash point of greater than 40° C., for example above 80° C. and more particularly above 100° C. Such solvents may be found for example in the class of alkyl, aralkyl or aryl esters of organic acids.

Thus according to a further aspect of the present invention there is provided an aqueous composition comprising an agrochemical, one or more foam-inducing surfactants and a water-insoluble antifoam agent wherein the antifoam agent is incorporated into the composition as a solution in an organic solvent wherein the organic solvent (a) dissolves a typical silicone antifoam such as Antifoam MSA to the extent of greater than 12% by weight, for example greater than 15% by weight; (b) provides a solution of the antifoam having a density of greater than 0.8 g/ml, for example from 0.8 to 1.1 g/ml; and (c) has a flash point of greater than 40° C., for example greater than 80° C. and more particularly greater than 100° C.

Examples of suitable solvents meeting the above criteria are alkyl, aralkyl or aryl esters of an organic acid. Suitable ester esters of organic acid include $C_{1-10}$ alkyl esters of saturated and unsaturated fatty acids wherein the fatty acid contains for example from 10 to 25 carbon atoms, including mixtures of such esters present in natural fats. Specific examples include $C_{1-10}$ alkyl esters of lauric acid, myristic acid, palmitic acid, stearic acid, coconut oil, tallow oil and rape oil. Further examples include $C_{1-10}$ alkyl esters or diesters of dicarboxylic acids containing from 2 to 6 carbon atoms in the alkyl chain such as adipic acid. Further examples include $C_{1-10}$ alkyl esters of aryl acids such as benzoic acid. Further examples include $C_{8-12}$ alkyl esters of acetic acid or $C_{1-4}$ alkoxy substituted $C_{1-10}$ alkyl esters of acetic acid or heterocyclic $C_{4-10}$ esters of acetic acid or aralkyl esters of acetic acid. Further examples include $C_{5\ to\ 20}$ fatty acid diesters of propylene glycol or aryl diesters of propylene gycol. Further examples include esters of cyclic acid derivatives such as lactones.

Specific esters of organic esters, which may be mentioned, include methylated rape oil, diisooctyl adipate, diisopropyl adipate, isooctyl palmitate, isopropyl palmitate, butyl stearate, C8/C10 fatty acid methyl esters, n-butylbenzoate, methoxypropanol acetate, methyl oleate, isopropyl myristate, heptyl acetate, nonyl acetate, diethyl phthalate, dibutyl phthalate, di-isopropyl adipate, $C_8/C_{10}$ fatty acid diester of propylene glycol, dibutyl adipate, gamma butyrolactone, hexyl acetate, tetrahydrofurfuryl acetate, isobornyl acetate, dipropyleneglycol dibenzoate, benzylacetate, butyldiglycol acetate, hexyl benzoate, isobutyl acetoacetate, benzyl acetate, and ethyl lactate.

We have found that isopropyl myristate, butyl cocoate and butyl laurate, all of which have a density 0.85 g/ml and a flash point greater than 110° C., are particularly suitable for use as solvents in the present invention. Surprisingly, whilst the solubility of these solvents in de-ionised water is of the order of only 0.12 g/l, the solvent appears virtually miscible (or at least very finely dispersed) in an agrochemical concentrate composition such as a glyphosate aqueous concentrate. Agrochemical aqueous concentrates containing an alkylpolyglycoside as the bioperformance enhancing surfactant appear to be particularly effective in assisting the dispersal of the solution of the antifoam in the aqueous medium.

It is an advantage if the solution of the antifoam agent in the solvent has a lower viscosity than that of the antifoam agent alone since this may aid dispersion. The viscosity of the antifoam agent is typically 500 to 2000 mPas and that of the solution of the antifoam agent in the solvent is preferably from 10 mPas to 1000 mPas, most preferred 10 to 200 mPas.

We have further found that, surprisingly, the adhesion of silicone antifoams such as antifoam MSA when in solution with effective solvents such as isopropylmyristate, is reduced with respect to plastic and metal surfaces. Silicone antifoams have a tendency to adhere to plastic and metal surfaces, which can affect surface cleaning procedures, whereas the viscosity reducing effect and interfacial change of adding the solvent significantly enhances the removal of the antifoam.

The solution of the antifoam in the solvent may be added directly to the aqueous agrochemical formulation or may if desired be pre-emulsified into water prior to incorporation in the aqueous agrochemical formulation. We have found that the solution of the antifoam agent in the solvent is generally readily incorporated into a pre-emulsion or directly into the agrochemical aqueous composition by conventional techniques such as stirring or shaking. It will be appreciated however that it is not necessary that the solution of the antifoam agent in the solvent is added to the finished agrochemical aqueous formulation, but may alternatively be added during the formulation process. It is to be understood therefore that the expression "incorporated" into the aqueous agrochemical composition as used herein includes a composition in which the solution of the antifoam agent in the solvent is added during the process of formulation of the agrochemical composition rather than to the finished aqueous agrochemical composition.

Thus according to a further aspect of the present invention there is provided a method of reducing the foaming of an agrochemical composition which comprises introducing an antifoam into the composition in the form of a solution in an organic solvent.

If desired, the solution of the antifoam agent in the solvent may first be mixed with some or all of the surfactants or adjuvants to be utilised in the agrochemical composition and the blend may thereafter emulsified into a solution of the agrochemical in water or into water with the subsequent addition of the water-soluble agrochemical. The formation of an aqueous emulsion of the solution of the antifoam agent in the solvent may be assisted by conventional emulsifying agents. Such agents may already be present in the agrochemical formulation as bioperformance enhancing agents or otherwise or may be added as additional emulsifying agents, for example by incorporation directly in the solution of the antifoam agent in the solvent.

Numerous examples of suitable emulsifying agents will occur to those skilled in the art. Typical examples have a HLB in the range of 8-18 where the HLB is defined as the "hydrophile-lipophile balance" as introduced and described by Atlas Chemical Industries, Inc. in the 1940s. Typical of the many examples are (polyoxyethylene) sorbitan alkyl esters; alkylphenol ethoxylates such as tristyrylphenol ethoxylate and tributylphenol ethoxylate; alcohol alkoxylates from synthetic and natural alcohol sources such as SYNPERONIC 13/6.5, RENEX 30, RENEX 36 and BRIJ 92; block co-polymers such as PEO/PPO block co-polymers; fatty acid alkoxylates; alkylpolyglycosides; alkaline metal alkylbenzene sulfonates; and blends of the above.

Once formed, we have found that the emulsified antifoam agent within the finished agrochemical product remains stable in suspension for a surprisingly long period compared with the conventional approach using the silicone antifoam alone. The long-term stability may be enhanced by the presence of further surfactants and we have found that cationic surfactants or non-ionic surfactants that take on cationic characteristics at the pH of the composition are particularly effective. Examples of such cationic surfactants include alkylamine ethoxylates such as GENAMIN C050, ETHOMEEN C15, ETHOMEEN T25, GENAMIN T150; etheramine ethoxylates; and the JEFFAMINE range of cationic surfactants such as JEFFAMINE D400, ED600.

In some instances the cationic surfactant may have a role both as a bioperformance enhancing adjuvant for the agrochemical active ingredient and to stabilise the antifoam agent against separation from the aqueous phase.

It is to be understood that the composition of the present invention will not necessarily be immune from separation of the antifoam agent over extended periods and/or under extreme conditions of temperature. However, even if not fully overcome under all adverse circumstances, the problem of separation of the antifoam agent is much reduced by the process of the present invention.

If desired suitable gelling agents such as polysaccharide additives may be incorporated in the compositions of the present invention with the intention of further reducing the tendency of the antifoam to undergo separation. Examples include KELZAN, KELZAN ASX and RHODOPOL 23.

The invention is illustrated by the following Examples in which all parts and percentages are by weight unless otherwise stated.

The following is a description of the products indicated by their trade names in the Examples.

| Chemical name | Description | Supplier/CAS Number |
| --- | --- | --- |
| Genamin C050 * | Polyoxyethylene(5)cocoamine | Clariant, 61791-14-8 |
| Genapol X080 * | Polyoxyethylene(8)isotridecylamine | Clariant, 9043-30-5 |
| AL2575 * | Octyl/decyl polyglycoside | Uniqema, 68515-73-1 |
| Antifoam MSA * | Polydimethylsilicone preparation | Dow |
| Waxoline Green | High strength, polymer soluble dye | Avecia Pigments and Additives Ltd |
| Tween 20 * | Polyoxyethylene(20)sorbitan laurate | Uniqema |
| Tween 40 * | Polyoxyethylene(20)sorbitan palmitate | Uniqema |
| Span 85 * | Sorbitan trioleate | Uniqema |
| Tween 80 * | Polyoxyethylene(20)sorbitan oleate | Uniqema |
| Fluowet PL80 * | Perfluorinated phosphinic/phosphonic acid | Clariant |
| Aerosol OT-B * | Sodium salt of di-octyl sulpho-succinic acid | See WO 02/076212 |
| Atlas G-5000 * | Alkyl propoxylate ethoxylate block co-polymer | Uniqema |
| Sulfacide Blue 5J | Liquid blue dye | See WO 02/076212 |
| Manutex RM * | Sodium Alginate | See WO 02/076212 |
| Ethomeen T25 * | Polyoxyethylene(5)tallowamine | Akzo Nobel, 61791-25-1 |
| PP796 | Emetic | See WO 02/076212 |
| Pyridine bases H | Mixture of pyridine bases | See WO 02/076212 |
| Nansa 1169A | Sodium salt of dodecyl benzene sulphonate | See WO 02/076212 |
| Renex 30 * | Polyoxyethylene derivative of highly branched synthetic aliphatic alcohol | Uniqema |
| Renex 36 * | Polyoxyethylene derivative of highly branched synthetic aliphatic alcohol | Uniqema |
| Synperonic 13/6.5 * | Polyoxyethylene derivative of highly branched synthetic aliphatic alcohol | Uniqema |
| Rhodorsil Silcolapse 5020 * | Silicone antifoam composition | Rhodia |
| Soprophor FLK * | Potassium Salt of Tristyrylphenol Ethoxylate Phosphate Ester | Rhodia, 163436-84-8 |

-continued

| Chemical name | Description | Supplier/CAS Number |
|---|---|---|
| Butyl cocoate | Butyl ester of fatty acid derived from coconut oil | Commodity chemical |
| Isopropylmyristate | Isopropyl ester of myristic acid | Commodity chemical |

* Tradename of the indicated supplier.

EXAMPLES

General Methodology

An aqueous agrochemical sample, including surfactant and antifoam, was prepared in a quantity typically of 200 to 300 grams. To the aqueous agrochemical sample containing the indicated surfactants was added a pre-prepared antifoam/solvent/emulsifier solution with shaking or mixing. The agrochemical product containing the antifoam was then stored in a 250 ml plastic container. A sample was taken initially from the homogenized sample and the container was then allowed to stand. Samples were subsequently from the bottom of the container at various time periods as indicated in the Example. The relevant sub-sample was then subjected to a foam test. Sampling and testing in this way determines the extent to which the antifoam has risen upwards in the sample, as governed by Stokes' Law.

Foam Test

An adaptation of the standard test CIPAC MT 47.2 was used to measure the extent of foaming. The previously prepared agrochemical concentrate was diluted using 5% v/v of the aqueous agrochemical concentrate and 95% v/v local tap water. A measuring cylinder (British Standard 604 type) was filled with 190 ml of tap water to which 10 ml of aqueous agrochemical concentrate was added. The cylinder was stoppered and inverted 30 times and placed upright on the bench. The volume of foam generated in the cylinder head space, which can accommodate up to 100 milliliters of foam as a maximum was measured. The foam volume data is quoted at seconds, 60 seconds, 180 seconds and 12 minutes after completion of the 30 inversions.

Examples 1 to 4

Antifoam MSA solution in butyl cocoate (with emulsifier where indicated) was added to an aqueous glyphosate concentrate containing glyphosate potassium salt, the adjuvant AL2575 and the adjuvant Genamin CO50 and then water was added as required to give a final concentration of 500 g/l glyphosate expressed as the glyphosate acid equivalent, 172.2 g/l of adjuvant AL2572 and 46.4 g/l of the adjuvant Genamin CO50. The density of the aqueous agrochemical composition without antifoam and solvent was =1.37 g/ml. In each case sufficient of the antifoam solution was added to give a concentration of Antifoam MSA in the final composition of 0.5 g/l. The composition of the antifoam MSA solution in added to the glyphosate concentrate is given in the following Table (I). In this particular experiment each solution contained from 0.02 to 0.05 g/l Waxoline Green as a dye to assist in visualising the antifoam emulsion droplets.

TABLE I

| Example No | Butyl Cocoate Conc. % w/w | Antifoam MSA Conc. % w/w | Emulsifier | Emulsifier Conc. % w/w | Density of antifoam solution, g/ml |
|---|---|---|---|---|---|
| 1 | 80.95 | 16.00 | Atlas G5000 | 3.00 | 0.87 |
| 2 | 79.70 | 15.75 | Soprophor FLK | 1.50 | 0.88 |
|  |  |  | Atlas G5000 | 3.00 |  |
| 3 | 70 | 30 | — | — | 0.89 |
| 4 | 66.78 | 13.2 | Tween 40 | 15 | 0.88 |
|  |  |  | Span 85 | 5 |  |

The antifoam premix indicated in Table I was added directly to the glyphosate concentrate (typically, 200 to 300 gram batch size) and incorporated by vigorous manual shaking for 30 seconds. Once the solution of antifoam was fully dispersed in the glyphosate concentrate, the samples were tested for foaming using the general method given above and the results are given in Tables II and III. Comparison 1 is the agrochemical concentrate without the addition of any antifoam and Comparison 2 is the agrochemical concentrate with the addition of 0.5 g/l Antifoam MSA without a solvent or additional emulsifiers.

TABLE II

Initial foam test data at 1 hour after preparation of an homogenised sample

| Example | Foam (ml) at | | | |
|---|---|---|---|---|
|  | 10 s | 1 min | 3 min | 12 min |
| Comparison 1 | 100 | 90 | 70 | 10 |
| Comparison 2 | 20 | 0 | 0 | 0 |
| Example 1 | 100 | 10 | 2 | 0 |
| Example 2 | 100 | 10 | 2 | 0 |
| Example 3 | 100 | 10 | 4 | 4 |
| Example 4 | 80 | 0 | 0 | 0 |

TABLE III

Foam test data after the samples had been left standing undisturbed for 48 hours; sub-samples were taken from the bottom of the container

| | Foam (ml) at | | | |
|---|---|---|---|---|
|  | 10 s | 1 min | 3 min | 12 min |
| Comparison 2 | 100 | 90 | 50 | 10 |
| Example 1 | 100 | 10 | 0 | 0 |
| Example 2 | 100 | 6 | 0 | 0 |
| Example 3 | 100 | 6 | 3 | 0 |
| Example 4 | 100 | 8 | 4 | 0 |

No visible separation by naked eye of the antifoam MSA oil was observed in any of the Examples of the invention. Comparison 2 showed significant visual separation.

Examples 5 to 17

Antifoam MSA solution in isopropyl myristate (with emulsifier where indicated) was added to an aqueous glyphosate concentrate containing glyphosate potassium salt, the adjuvant AL2575 and the adjuvant Genamin CO50 and then water was added as required to give a final concentration of 500 g/l glyphosate expressed as the glyphosate acid equivalent, 172.2 g/l of adjuvant AL2572 and 46.4 g/l of the adjuvant Genamin CO50. In each case sufficient of the solution was added to give a concentration of Antifoam MSA in the final composition of 0.5 g/l. The composition of the antifoam MSA solution in added to the glyphosate concentrate is given in the following Table (IV).

TABLE IV

| Example No | Isopropyl-myristate Conc. % w/w | Antifoam MSA Conc. % w/w | Emulsifier | Emulsifier Conc. % w/w | Density of antifoam solution, g/ml |
|---|---|---|---|---|---|
| 5 | 84.00 | 16.00 | — | — | 0.87 |
| 6 | 66.80 | 13.20 | Tween 20 | 15.00 | 0.90 |
|   |       |       | Span 85  | 5.00  |      |
| 7 | 66.80 | 13.20 | Tween 40 | 15.00 | 0.90 |
|   |       |       | Span 85  | 5.00  |      |
| 8 | 66.80 | 13.20 | Tween 80 | 15.00 | 0.90 |
|   |       |       | Span 85  | 5.00  |      |
| 9 | 81.00 | 16.00 | Tween 20 | 3.00  | 0.88 |
| 10 | 81.00 | 16.00 | Span 85 | 3.00 | 0.88 |
| 11 | 81.00 | 16.00 | Tween 40 | 3.00 | 0.88 |
| 12 | 81.00 | 16.00 | Tween 80 | 3.00 | 0.88 |
| 13 | 83.50 | 16.00 | Span 85 | 0.50 | 0.87 |
| 14 | 83.00 | 16.00 | Span 85 | 1.00 | 0.87 |
| 15 | 82.50 | 16.00 | Span 85 | 1.50 | 0.87 |
| 16 | 82.00 | 16.00 | Span 85 | 2.00 | 0.87 |
| 17 | 81.50 | 16.00 | Span 85 | 2.50 | 0.87 |

The antifoam premix indicated in Table IV was added directly to the glyphosate concentrate (typically, 200 to 300 gram batch size) and incorporated by vigorous manual shaking for 30 seconds. Once the solution of antifoam was fully dispersed in the glyphosate concentrate, the samples were tested for foaming using the general method given above and the results are given in Tables V and VI. Comparison 3 is the agrochemical concentrate without the addition of any antifoam and Comparison 4 is the agrochemical concentrate with the addition of 0.5 g/l Antifoam MSA without a solvent or additional emulsifiers.

TABLE V

Initial foam test data at 1 hour after preparation of an homogenised sample

| Example | Foam (ml) at | | | |
|---|---|---|---|---|
|   | 10 s | 1 min | 3 min | 12 min |
| Comparison 3 | 100 | 90 | 70 | 10 |
| Comparison 4 | 30 | 0 | 0 | 0 |
| Example 5 | 50 | 4 | 2 | 0 |
| Example 6 | 90 | 8 | 4 | 0 |
| Example 7 | 90 | 2 | 0 | 0 |
| Example 8 | 90 | 2 | 0 | 0 |
| Example 9 | 50 | 4 | 2 | 0 |
| Example 10 | 90 | 8 | 8 | 2 |
| Example 11 | 40 | 2 | 1 | 0 |
| Example 12 | 90 | 6 | 4 | 0 |
| Example 13 | 30 | 4 | 2 | 0 |
| Example 14 | 30 | 2 | 2 | 0 |
| Example 15 | 30 | 2 | 0 | 0 |
| Example 16 | 50 | 4 | 2 | 0 |
| Example 17 | 30 | 2 | 0 | 0 |

TABLE VI

Foam test data after the samples had been left standing undisturbed for 48 hours; sub-samples were taken from the bottom of the container

| | Foam (ml) at | | | |
|---|---|---|---|---|
|   | 10 s | 1 min | 3 min | 12 min |
| Comparison 3 | 100 | 90 | 70 | 10 |
| Comparison 4 | 100 | 90 | 10 | 10 |
| Example 5 | 90 | 4 | 4 | 0 |
| Example 6 | 90 | 6 | 4 | 0 |
| Example 7 | 90 | 6 | 2 | 0 |
| Example 8 | 90 | 4 | 2 | 0 |
| Example 9 | 60 | 4 | 2 | 0 |
| Example 10 | 90 | 8 | 6 | 0 |
| Example 11 | 40 | 2 | 0 | 0 |
| Example 12 | 90 | 6 | 4 | 0 |
| Example 13 | 50 | 4 | 2 | 0 |
| Example 14 | 40 | 2 | 0 | 0 |
| Example 15 | 40 | 3 | 0 | 0 |
| Example 16 | 60 | 4 | 0 | 0 |
| Example 17 | 60 | 4 | 0 | 0 |

No visible separation by eye of the antifoam MSA oil was observed in any of the Examples of the invention. Significant separation observed for Comparison 4.

TABLE VII

Foam test data after the samples had been left standing undisturbed for 30 days; sub-samples were taken from the bottom of the container

| | Foam (ml) at | | | |
|---|---|---|---|---|
|   | 10 s | 1 min | 3 min | 2 min |
| Comparison 3 | 100 | 90 | 70 | 10 |
| Comparison 4 | 100 | 90 | 40 | 10 |
| Example 5 | 90 | 12 | 6 | 0 |
| Example 6 | 100 | 20 | 10 | 2 |
| Example 7 | 90 | 15 | 6 | 0 |
| Example 8 | 90 | 10 | 2 | 0 |
| Example 9 | 90 | 12 | 6 | 0 |
| Example 10 | 90 | 14 | 8 | 0 |
| Example 11 | 90 | 6 | 4 | 0 |
| Example 12 | 90 | 8 | 6 | 0 |
| Example 13 | 90 | 14 | 8 | 0 |
| Example 14 | 90 | 20 | 8 | 0 |
| Example 15 | 90 | 8 | 4 | 0 |
| Example 16 | 100 | 12 | 8 | 0 |
| Example 17 | 90 | 12 | 6 | 0 |

Example 18

The composition of Example 15 was prepared at the 5 liter scale, except that 0.6 g/L antifoam MSA was incorporated via the antifoam MSA solution in this Example. To this end, 15.7 g of the antifoam solution of Example 15 (Table IV) were added into an empty 5 liter plastic container. Further, 6.8 Kg of the potassium glyphosate agrochemical concentrate (Examples 5 to 17) were added and the antifoam incorporated by vigorous manual shaking for 300 seconds. A control sample was also prepared where the antifoam MSA alone (3 g) was added to 6.8 kg of the potassium glyphosate agrochemical concentrate using the same methodology.

Assessment of foaming characteristics was carried out using a purpose-built glass 12 liter sprayer. The aqueous agrochemical concentrate (50 ml) was added into 5 liters of water within a glass cylinder. The solution was re-circulated by a pump to give a mixing regime in which foam was easily formed. The foam height was monitored during the mixing procedure at the indicated times during the mixing. The composition was then sprayed and the foam height was measured after all of the composition had been sprayed out of the glass cylinder. Finally, 3 liters of water were poured into the glass vessel to simulate clean down and the final foam height was measured. The results are given in Table VIII.

TABLE VIII

Foam Test Data

| Description of test | Foam height (cm) at | | | |
|---|---|---|---|---|
| | 1 min | 5 min | End of spraying | Re-fill |
| CONTROL-after 5 days, sample from bottom of the 5 liter container | 35 | >50 | >50 | >50 |
| After 5 days, sample from the bottom of the 5 liter container | 3 | 4 | 5 | 1 |
| After 5 days, sample from the top of the 5 liter container | 4 | 4 | 5 | 1 |
| After 45 days, sample from the bottom of the 5 liter container | 4 | 4.5 | 3 | 2 |
| After 63 days, sample from the bottom of the 5 liter container | 8 | 11 | 13 | 7 |
| After 109 days, sample from the bottom of the 5 liter container | 8.5 | 11.5 | 10 | 6 |

Examples 19 to 29

Antifoam MSA solution in isopropyl myristate was added to provide an aqueous glyphosate concentrate containing glyphosate ammonium salt (360 g/l expressed as the glyphosate acid equivalent) 172.2 g/l of the adjuvant AL2575, 140 g/l of ammonium sulphate and 0.7 g/l of Fluowet PL80. At the concentration concerned Fluowet PL80 is water miscible. It is effective as a bulk defoamer only and does not suffer from a tendency to separate.

The density of the composition without antifoam and solvent was 1.27 g/ml. In each case sufficient of the Antifoam MSA solution was added to give a concentration of Antifoam MSA in the final composition of 1.0 g/l. The composition of the antifoam MSA solution in added to the glyphosate concentrate is given in the following Table (IX).

TABLE IX

| Example No | Isopropyl-myristate Conc. % w/w | Antifoam MSA Conc. % w/w | Emulsifier | Emulsifier Conc. % w/w | Density of antifoam solution, g/ml |
|---|---|---|---|---|---|
| 19 | 84.00 | 16.00 | — | — | 0.87 |
| 20 | 66.80 | 13.20 | Tween 20 Span 85 | 15.00 5.00 | 0.90 |
| 21 | 66.80 | 13.20 | Tween 40 Span 85 | 15.00 5.00 | 0.90 |
| 22 | 66.80 | 13.20 | Tween 80 Span 85 | 15.00 5.00 | 0.90 |
| 23 | 81.00 | 16.00 | Span 85 | 3.00 | 0.88 |
| 24 | 81.00 | 16.00 | Tween 80 | 3.00 | 0.88 |
| 25 | 83.50 | 16.00 | Span 85 | 0.50 | 0.87 |
| 26 | 83.00 | 16.00 | Span 85 | 1.00 | 0.87 |
| 27 | 82.50 | 16.00 | Span 85 | 1.50 | 0.87 |
| 28 | 82.00 | 16.00 | Span 85 | 2.00 | 0.87 |
| 29 | 81.50 | 16.00 | Span 85 | 2.50 | 0.87 |

The antifoam premix indicated in Table IX was added directly to the glyphosate concentrate (typically, 200 to 300 gram batch size) and incorporated by vigorous manual shaking for 30 seconds. After incorporation of the antifoam, the samples were tested for foaming using the general method given above and the results are given in Tables X and XI. Comparison 5 is the agrochemical concentrate without the addition of any antifoam and Comparison 6 is the agrochemical concentrate with the addition of 1.0 g/l Antifoam MSA without a solvent or additional emulsifiers.

TABLE X

Initial foam test data at 1 hour after preparation of an homogenised sample

| Example | Foam (ml) at | | | |
|---|---|---|---|---|
| | 10 s | 1 min | 3 min | 12 min |
| Comparison 5 | 100 | 100 | 90 | 60 |
| Comparison 6 | 90 | 90 | 80 | 10 |
| Example 19 | 90 | 30 | 12 | 10 |
| Example 20 | 60 | 8 | 6 | 4 |
| Example 21 | 20 | 4 | 2 | 0 |
| Example 22 | 60 | 4 | 2 | 2 |
| Example 23 | 90 | 10 | 6 | 6 |
| Example 24 | 50 | 6 | 6 | 4 |
| Example 25 | 90 | 40 | 10 | 8 |
| Example 26 | 90 | 80 | 30 | 18 |
| Example 27 | 90 | 50 | 10 | 10 |
| Example 28 | 90 | 80 | 60 | 20 |
| Example 29 | 90 | 90 | 40 | 30 |

TABLE XI

Foam test data after the samples had been left standing undisturbed for 23 days; sub-samples were taken from the bottom of the container

| | Foam (ml) at | | | |
|---|---|---|---|---|
| | 10 s | 1 min | 3 min | 12 min |
| Comparison 5 | 90 | 90 | 90 | 60 |
| Comparison 6 | 90 | 90 | 90 | 40 |
| Example 19 | 100 | 100 | 90 | 40 |
| Example 20 | 100 | 100 | 80 | 36 |
| Example 21 | 100 | 100 | 90 | 44 |
| Example 22 | 100 | 90 | 40 | 30 |
| Example 23 | 100 | 100 | 90 | 30 |
| Example 24 | 100 | 90 | 40 | 30 |
| Example 25 | 100 | 100 | 80 | 40 |
| Example 26 | 100 | 100 | 90 | 40 |
| Example 27 | 100 | 100 | 90 | 40 |
| Example 28 | 100 | 100 | 90 | 50 |
| Example 29 | 100 | 100 | 90 | 40 |

Example 30

Antifoam solutions were added to the paraquat dichloride concentrate composition described in Example 13 (Concentrate A) and Example 11 (Concentrate B) of WO 02/076212. The density of composition without antifoam or solvent was 1.15 g/ml. It should be noted that the composition of Example 13 already contains a small proportion of antifoam (0.25 g/l). This is added mainly to reduce foaming during manufacture and, as illustrated in the comparisons, has little affect in reducing the foaming of the diluted product.

In each case sufficient of the solution was added to give a concentration of antifoam in the final composition of 0.5 g/l. In this Example, two different silicone antifoams were used with Span 85 as emulsifier. The composition of the antifoam solution in/added to the paraquat concentrate is given in the following Table (XII) as Antifoam solutions A and B.

TABLE XII

| Antifoam Solution No | Isopropyl-myristate Conc. % w/w | Antifoam | Antifoam conc. % w/w | Emulsifier (Span 85) Conc. % w/w | Density of antifoam solution, g/ml |
|---|---|---|---|---|---|
| A | 82.5 | Antifoam MSA | 16 | 1.5 | 0.87 |
| B | 82.5 | Antifoam DB 100 | 16 | 1.5 | 0.87 |

The antifoam premix indicated in Table XII was added directly to the paraquat concentrate (typically, 200 to 300 gram batch size) and incorporated by vigorous manual shaking for 30 seconds. After the premix was incorporated, the samples were tested for foaming using the standard test. The results are given in Table XIII

TABLE XIII

Foam test data at various time periods

| | Foam (ml) at | | | |
|---|---|---|---|---|
| | 10 s | 1 min | 3 min | 12 min |
| Concentrate A-no antifoam added, | 120 | 120 | 110 | 40 |
| Concentrate B-no antifoam added, | 110 | 100 | 90 | 80 |
| Concentrate (A) with Antifoam Solution (A)-initial result | 80 | 60 | 30 | 30 |
| Concentrate (A) with Antifoam Solution (A)-After 5 days | 30 | 30 | 20 | 20 |
| Concentrate (A) with Antifoam Solution (B)-initial result | 60 | 60 | 20 | 20 |
| Concentrate (A) with Antifoam Solution (B)-After 5 days | 50 | 20 | 20 | 10 |
| Concentrate (B) with Antifoam solution (A)-initial result | 20 | 0 | 0 | 0 |
| Concentrate (B) with Antifoam Solution (A)-After 5 days | 30 | 20 | 20 | 20 |
| Concentrate (B) with Antifoam Solution (B)-initial result | 50 | 20 | 10 | 0 |
| Concentrate (B) with Antifoam Solution (B)-After 5 days | 30 | 20 | 20 | 10 |

Examples 31 to 33

This Example illustrates the manufacture of compositions according to the invention wherein the solution of the antifoam in isopropylmyristate is emulsified into water and the pre-formed emulsion is then added to an aqueous glyphosate concentrate.

Emulsions were prepared using the following method. The emulsifying agent(s) indicated in Table XIV were added to water and allowed to dissolve fully. The isopropylmyristate and the antifoam MSA (with Span 85 when used) were mixed to form a solution. The oil phase was added slowly to the water phase and mixed using a high shear mixer until the particle size was in the range 1-5 microns D(4,3) volume-weighted average as measured using a MALVERN MASTERSIZER® "S" laser particle sizing device.

Three emulsions (as indicated in Table XIV) were selected for testing in terms of foam performance in an aqueous potassium glyphosate agrochemical product containing glyphosate potassium salt (500 g/l expressed as the glyphosate acid equivalent) 165 g/l of the adjuvant AL2575, 44.4 g/l of the adjuvant Genamin CO50 and 2.63 g/l of the adjuvant Genapol X080. In each case sufficient of the emulsion was added to give a concentration of Antifoam MSA in the final composition of 0.5 g/l.

TABLE XIV

| Example No | Isopropyl-myristate Conc. % w/w | Antifoam MSA Conc. % w/w | Emulsifier | Emulsifier Conc. % w/w | Water |
|---|---|---|---|---|---|
| 31 | 33.5 | 6.5 | Renex 30 | 5.0 | To 100% |
|  |  |  | Renex 36 | 5.0 |  |
| 32 | 33.5 | 6.5 | Synperonic 13/6 | 10.0 | To 100% |
| 33 | 41.25 | 8.0 | Span 85 | 0.75 | To 100% |
|  |  |  | AL 2575 | 10.0 |  |

By way of a comparison, it should be noted that if the isopropylmyristate is replaced by water in the emulsion compositions of Table XIV, then the resulting emulsions cannot be processed whatsoever. An intractable oily mix of very large droplet size is produced in the SILVERSON® mixer vessel.

Note that in Example 33 the surfactant AL 2575 is both added as an emulsifying agent in the emulsion pre-mix and is present as an adjuvant in the glyphosate concentrate composition. The proportions were such that the concentration of AL 2575 in the final composition containing the antifoam emulsion was 165 g/l.

The antifoam emulsion was added to the glyphosate concentrate (250 gram batch size) and incorporated by manual shaking for 30 seconds. The samples were tested for foaming using the standard test. The results are given in Table XV.

TABLE XV

Foam test data at various time periods

| | Foam (ml) at | | | |
|---|---|---|---|---|
| | 10 s | 1 min | 3 min | 12 min |
| Comparison with no antifoam added | 100 | 90 | 70 | 10 |
| Comparison with antifoam added without solvent. Sampled from the bottom of the container after 48 hours | 100 | 90 | 50 | 10 |
| Example 31-initial result | 90 | 6 | 0 | 0 |
| Example 31-26 days | 100 | 30 | 0 | 0 |
| Example 31-73 days | 100 | 80 | 10 | 0 |
| Example 32-initial result | 80 | 6 | 0 | 0 |
| Example 32-26 days | 90 | 20 | 0 | 0 |
| Example 32-73 days | 100 | 50 | 8 | 6 |
| Example 33-initial result | 100 | 50 | 4 | 0 |
| Example 33-11 days | 100 | 80 | 10 | 0 |

Example 34

A solution of Antifoam MSA in isopropyl myristate was added to an aqueous concentrate containing potassium glyphosate at a concentration of 480 g/l based on glyphosate acid and the potassium salt of dicamba at a concentration of 7.5 g/l based on dicamba acid. In each case sufficient of the solution was added to give a concentration of antifoam in the final composition of 0.6 g/l. The composition of the antifoam solution added to the glyphosate/dicamba concentrate is given in Table (XVI).

TABLE XVI

| Isopropyl-myristate Conc. % w/w | Antifoam MSA Conc. % w/w | Emulsifier | Emulsifier Conc. % w/w | Density of antifoam solution, g/ml |
|---|---|---|---|---|
| 82.5 | 16.00 | Span 65 | 1.5 | 0.87 |

Table XVII gives the resultant foam data. The antifoam solution was added directly to the agrochemical concentrate (250 gram batch size) and incorporated by vigorous manual shaking for 30 seconds. In this Example, the agrochemical sample was stored at 40° C. rather than room temperature between the foam testing.

TABLE XVII

Foam test data at various time periods

| | Foam (ml) at | | | |
|---|---|---|---|---|
| | 10 s | 1 min | 3 min | 12 min |
| Sample without antifoam initially | 100 | 90 | 10 | 10 |
| Antifoam MSA added without solvent at 0.6 g/l-measured after 24 hours at ambient | 90 | 90 | 10 | 10 |
| Composition of the invention-initial result | 80 | 0 | 0 | 0 |
| Composition of the invention-after 24 hours at 40° C. | 70 | 0 | 0 | 0 |
| Composition of the invention-after 48 hours at 40° C. | 80 | 30 | 0 | 0 |
| Composition of the invention-after 19 days at 40° C. | 90 | 50 | 0 | 0 |
| Composition of the invention-after 30 days at 40° C. | 100 | 90 | 10 | 0 |

Examples 35 and 36

This Example illustrates the use of solvents selected such that the density of the solution of the antifoam differs from that of the agrochemical concentrate in the absence of solvent by no more than 0.05 g/ml density units.

The agrochemical concentrate was prepared and water added such that after the addition of the antifoam, the composition consisted of ammonium glyphosate at a concentration of 360 g/l based on glyphosate acid, the adjuvant AL 2575 at a concentration of 172.2 g/l, ammonium sulphate at a concentration of 140 g/l, Fluowet PL80 at a concentration of 0.7 g/l and Antifoam MSA at a concentration of 3.0 g/l. The density of the agrochemical concentrate in the absence of MSA and solvent was 1.28 g/ml. The antifoam solution was added last direct to the sample (typically, 200 to 300 gram batch size) and incorporated by vigorous manual shaking for 30 seconds. Sufficient solution was used to provide a concentration of Antifoam MSA in the concentrate of 3.0 g/l. In the Control sample, 3.0 g/l of Antifoam MSA was added without solvent. The samples were stored in a 250 milliliter plastic container. Two solvents for the antifoam were used. Solution A contained 84% w/w of 2-bromopropane and 16% w/w of Antifoam MSA. The density of Solution A was 1.29 g/ml at room temperature. Solution B contained 84% w/w of cyclohexyl bromide and 16% w/w of Antifoam MSA. The density of solution B was 1.27 g/ml at room temperature.

The assessment of foam characteristics was carried out using the purpose-built glass 12 liter sprayer and the method described in Example 18 The results are given in Table XVIII for Solution A (Example 35) and in Table XIX for Solution B (Example 36).

TABLE XVIII

Foam Test Data After Various Periods Of Storage Using Solution A

| | Foam height (cm) at | | | |
|---|---|---|---|---|
| | 1 min | 5 min | End of spraying | Re-fill |
| Control sample with Antifoam MSA and no solvent-after 3 days, sample from bottom of the container | — | 55 | 40 | — |
| Example 35-After 2 days, sample from the bottom of the container | — | 0 | 0 | — |
| Example 35-After 4 days, sample from the bottom of the container | — | 0 | 0 | — |
| Example 35-After 10 days, sample from the bottom of the container | — | 20 | 0 | — |
| Example 35-After 13 days, sample from the bottom of the container | — | 20 | 0 | — |

TABLE XIX

Foam Test Data After Various Periods Of Storage Using Solution B

| | Foam height (cm) at | | | |
|---|---|---|---|---|
| | 1 min | 5 min | End of spraying | Re-fill |
| Control sample with Antifoam MSA and no solvent-after 3 days, sample from bottom of the container | — | 55 | 40 | — |
| Example 36-After 2 days, sample from the bottom of the container | — | 0 | 0 | — |
| Example 36-After 4 days, sample from the bottom of the container | — | 0 | 0 | — |
| Example 36-After 7 days, sample from the bottom of the container | — | 20 | 0 | — |

The invention claimed is:

1. An aqueous agrochemical composition comprising at least one agrochemical, one or more foam-inducing surfactants and a water-insoluble liquid silicone-containing antifoam agent, wherein the water-insoluble liquid silicone-containing antifoam agent is incorporated into the composition as a solution in an organic solvent comprising at least one member selected from isopropyl myristate, butyl cocoate and butyl laurate, wherein the water-insoluble liquid silicone-containing antifoam agent is present in the organic solvent at a concentration of at least 10% by weight, said at least one agrochemical comprising at least one member selected from glyphosate, paraquat, diquat, dicamba, fomesafen, imazethapyr, imazaquin, imazapyr, 2,4-D and glufosinate.

2. An aqueous composition according to claim 1 wherein the water-insoluble liquid silicone-containing antifoam agent comprises a polyalkylsilicone.

3. An aqueous composition according to claim 2 wherein the water-insoluble liquid silicone-containing antifoam agent further comprises hydrophobic silicas.

4. An aqueous composition according to claim 1 wherein the organic solvent has a flash point of greater than 40° C.

5. An aqueous composition according to claim 1 further comprising a bioperformance enhancing agent.

6. An aqueous composition according to claim 5, wherein the bioperformance enhancing agent comprises an alkylpolyglycoside.

7. An aqueous composition according to claim 1 wherein the agrochemical comprises at least one water-soluble agrochemical.

8. An aqueous concentrate composition according to claim 1, further comprising an emulsifying agent.

9. An aqueous composition according to claim 8, wherein the emulsifying agent comprises a sorbitan alkyl ester, a polyoxyethylene sorbitan alkyl ester, an alkylphenol ethoxylate, an alcohol alkoxylate, a block co-polymer, a fatty acid alkoxylate, an alkylpolyglycoside, an alkaline metal alkylbenzene sulfonate, or any blend thereof.

10. An aqueous composition according to claim 1, further comprising a polysaccharide additive.

11. An aqueous composition according to claim 1, further comprising a bioperformance enhancing agent comprising an alkylpolyglycoside.

12. An aqueous concentrate composition comprising an agrochemical, one or more foam-inducing surfactants and a water-insoluble liquid silicone-containing antifoam agent,
wherein the water-insoluble liquid silicone-containing antifoam agent is incorporated into the composition as a solution in an organic solvent comprising at least one member selected from isopropyl myristate, butyl cocoate and butyl laurate;
said at least one agrochemical comprising at least one member selected from glyphosate, paraquat, diquat, dicamba, fomesafen, imazethapyr, imazacquin, imazapyr, 2,4-D and glufosinate, and
wherein the organic solvent is selected such that a density of the solution of the water-insoluble liquid silicone-containing antifoam agent in the organic solvent differs from a density of the aqueous concentrate composition measured in the absence of the organic solvent and water-insoluble liquid silicone-containing antifoam by not more than 0.1 g/l density units, all density measurements being conducted at room temperature.

13. An aqueous concentrate composition according to claim 12 wherein the agrochemical comprises at least one water-soluble agrochemical.

14. An aqueous concentrate composition according to claim 12, wherein the water-insoluble liquid silicone-containing antifoam agent is present in the organic solvent at a concentration of at least 10% by weight.

15. An aqueous composition comprising an agrochemical, one or more foam-inducing surfactants and a water-insoluble liquid silicone-containing antifoam agent,
wherein the water-insoluble liquid silicone-containing antifoam agent is incorporated into the composition as a solution in an organic solvent, wherein the organic solvent is an alkyl ester, selected from the group consisting of isopropyl myristate, butyl cocoate and butyl laurate;
said agrochemical comprising at least one member selected from glyphosate, paraquat, diquat, dicamba, fomesafen, imazethapyr, imazaquin, imazapyr, 2,4-D and glufosinate;
wherein said ester (a) contains the water-insoluble liquid silicone-containing antifoam at a concentration of greater than 12% by weight; and (b) provides a solution of the water-insoluble liquid silicone-containing antifoam having a density of greater than 0.8 g/ml; and (c) has a flash point of greater than 40° C.

16. An aqueous concentrate composition according to claim 15, wherein said aqueous composition, prior to addition of said solution of the water-insoluble liquid silicone-containing antifoam, has a density ranging from above 1 g/ml to 1.4 g/ml.

17. An aqueous concentrate composition according to claim 16, wherein said agrochemical comprises glyphosate, and said aqueous composition, prior to addition of said solution of the water-insoluble liquid silicone-containing antifoam, has a density ranging from 1.2 g/ml to 1.4 g/ml.

18. A method of reducing foaming of an aqueous agrochemical composition comprising at least one agrochemical, said method comprising
introducing a water-insoluble liquid silicone-containing antifoam into the composition in the form of a solution in an organic solvent comprising at least one member selected from isopropyl myristate, butyl cocoate and butyl laurate;
said agrochemical comprising at least one member selected from glyphosate, paraquat, diquat, dicamba, fomesafen, imazethapyr, imazaquin, imazapyr, 2,4-D and glufosinate; and
wherein the water-insoluble liquid silicone-containing antifoam agent is present in the organic solvent at a concentration of at least 10% by weight.

19. A method for reducing or eliminating separation of a water-insoluble liquid silicone-containing antifoam in an aqueous agrochemical composition comprising at least one agrochemical, said method comprising
introducing a water-insoluble liquid silicone-containing antifoam into the aqueous agrochemical composition in the form of a solution in an organic solvent comprising at least one member selected from isopropyl myristate, butyl cocoate and butyl laurate;
wherein the at least one member selected from glyphosate, paraquat, diquat, dicamba, fomesafen, imazethapyr, imazaquin, imazapyr, 2,4-D and glufosinate, and
wherein the water-insoluble liquid silicone-containing antifoam agent has a solubility in the organic solvent of at least 10% by weight at a temperature in the range of 15-20° C.

20. The method according to claim 19 wherein the solution of the water-insoluble liquid silicone-containing antifoam in the solvent is added directly to the aqueous agrochemical composition, and wherein the water-insoluble liquid silicone-containing antifoam agent is present in the organic solvent at a concentration of at least 10% by weight.

21. The method according to claim 19 wherein the solution of water-insoluble liquid silicone-containing antifoam in the solvent is pre-emulsified into water prior to incorporation into the aqueous agrochemical composition, and wherein the water-insoluble liquid silicone-containing antifoam agent is present in the organic solvent at a concentration of at least 10% by weight.

* * * * *

UNITED STATES PATENT AND TRADEMARK OFFICE
CERTIFICATE OF CORRECTION

PATENT NO. : 7,994,095 B2  Page 1 of 1
APPLICATION NO. : 10/553914
DATED : August 9, 2011
INVENTOR(S) : Carl Formstone et al.

It is certified that error appears in the above-identified patent and that said Letters Patent is hereby corrected as shown below:

IN THE CLAIMS:

Col. 19, line 37, "imazacquin" should read "imazaquin".

Signed and Sealed this
Eighteenth Day of October, 2011

David J. Kappos
*Director of the United States Patent and Trademark Office*